United States Patent [19]

Patterson

[11] Patent Number: 4,586,380

[45] Date of Patent: May 6, 1986

[54] ULTRASONIC TRANSDUCER ASSEMBLY

[75] Inventor: Robert W. Patterson, Cobleskill, N.Y.

[73] Assignee: General Electric Company, Schenectady, N.Y.

[21] Appl. No.: 692,608

[22] Filed: Jan. 17, 1985

[51] Int. Cl.⁴ .............................................. G01N 29/04
[52] U.S. Cl. ........................................ 73/623; 73/640; 74/479
[58] Field of Search ................ 73/623, 634, 635, 637, 73/638, 639, 640; 324/220, 221; 248/184; 74/479

[56] References Cited

U.S. PATENT DOCUMENTS

| | | | |
|---|---|---|---|
| 3,949,292 | 4/1976 | Beaver et al. | 324/220 |
| 4,105,972 | 8/1978 | Smith | 73/638 |
| 4,166,395 | 9/1979 | Dannehl | 73/634 |
| 4,304,134 | 12/1981 | Rouse et al. | 73/634 |

*Primary Examiner*—Stephen A. Kreitman
*Attorney, Agent, or Firm*—Jerome C. Squillaro; Paul Checkovich

[57] ABSTRACT

A transducer assembly for maintaining a transducer in contact with, and in alignment with, a surface includes a pair of opposed swivel bars, each of which is pivotably mounted to a cradle. The swivel bars are free to pivot about a roll axis. Two tension arms are pivotably mounted to one of the swivel bars. Each tension arm resiliently urges an end of the transducer into contact with the surface. One of the swivel bars supports two spaced-apart wheels whose contact with the surface is effective to rotate its swivel bar into a predetermined rotation about the roll axis. The transducer, being attached to the swivel bar by one of the tension arms is also rotated into a predetermined angle about the roll axis.

17 Claims, 7 Drawing Figures

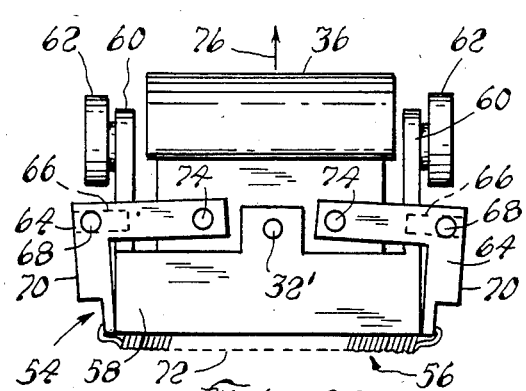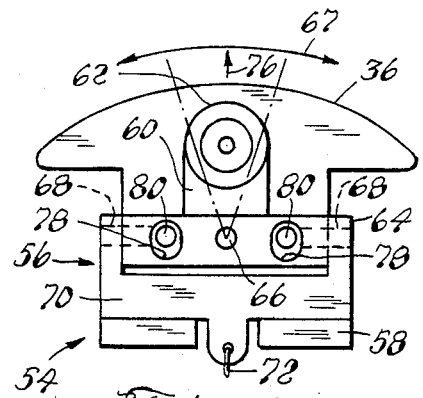
Fig. 2A PRIOR ART  Fig. 2B
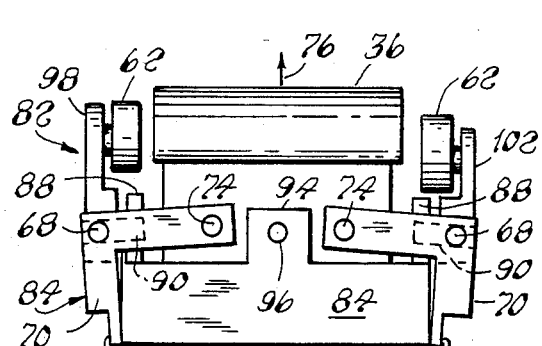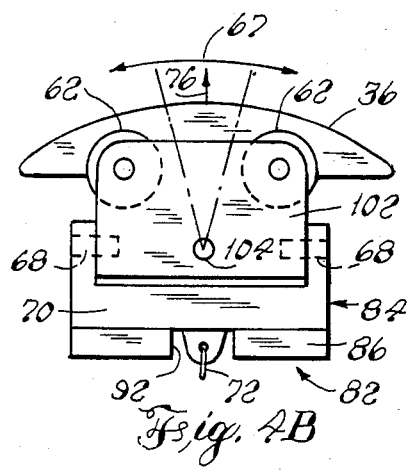
Fig. 4A  Fig. 4B
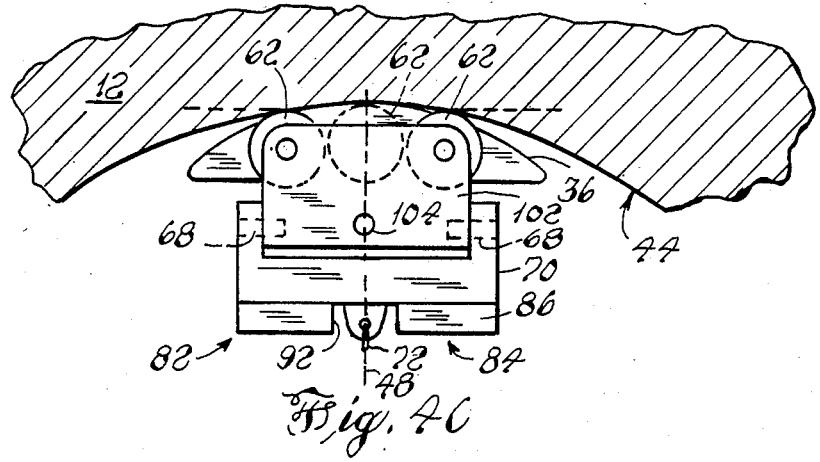
Fig. 4C

ULTRASONIC TRANSDUCER ASSEMBLY

The invention relates to ultrasonic testing apparatus and, more particularly, to apparatus for the rapid and automatic alignment of a transducer of an ultrasonic testing device.

Ultrasonic testing devices project ultrasonic energy into a large solid object to detect the presence of defects therein by the scattering and reflection of ultrasonic energy from the defects. Although ultrasonic testing devices may have other applications, for concreteness of description, the following discussion is directed to the use of such devices in testing the rotors of large steam turbines.

The rotor of a steam turbine may weigh as much as several hundred tons and may rotate at a speed of, for example, 3600 RPM. As a result of the large mass and the high rotational speed, such a rotor develops substantial stresses therein which are concentrated in the vicinity of the axis thereof. In time, such stresses may cause the development of cracks which, if not discovered and dealt with in a timely fashion, could eventually lead to failure of the rotor. The bore of the rotor forging tends to have a high concentration of flaws, due to segregation during cooling. In order to remove the most likely situs of flaws, voids and discontinuities, and in order to facilitate testing for such incipient defects, certain large steam turbines include axial bores therein which provide access for an axial ultrasonic testing device. Routine maintenance of a large steam turbine conventionally includes such axial ultrasonic testing. If a defect is discovered near the bore, it may be removed by enlarging the bore sufficiently to remove it. Less critical defects may merely be recorded and scheduled for critical attention on the next scheduled inspection.

An ultrasonic testing device includes a transducer which is inserted into the axial bore in the shaft. The transducer projects a beam of ultrasonic energy into the test object which continues in a straight line until it is scattered or reflected from a defect which may be, for example, a crack or an inclusion. Some of the scattered or reflected ultrasonic energy is returned to the transducer where its reception provides an indication of the existence of the defect. A knowledge of the position of the transducer within the bore at the time the reflected signal is received, as well as the transit time of the signal within the test object, is sufficient to locate the defect in three dimensions within the body of the turbine rotor. The operation of such ultrasonic testing devices is well known and described in the art. Accordingly, the principles of operation of ultrasonic testing devices are discussed herein only in detail necessary to permit understanding of the present invention.

A transducer used with an ultrasonic testing device has generally arcuate upper surface from which the ultrasonic waves used in the testing process propagate, and at which the ultrasonic waves returned from a discontinuity are received. The radius of the arcuate upper surface is generally slightly smaller than the radius of the inner surface of the bore in which the test is being performed. When the transducer is urged against the inner surface of the bore, the arcuate upper surface of the transducer meets the arcuate inner surface of the bore along a line of contact. It is common to find an axial bore in a turbine shaft that includes a number of different radii. In order to accommodate the different radii, an ultrasonic testing device may be provided with a plurality of interchangeable transducers having arcuate upper surfaces of varying radii. However, when changing transducers, an alignment procedure is necessary. The alignment procedure of the prior art ultrasonic transducer is difficult, time-consuming and requires highly skilled operators to perform.

The transducer must be aligned so that the line of contact made with the bore falls at a predetermined position on the arcuate upper surface of the transducer. A tube extending into the bore includes three angularly expandable legs at an inner end thereof. The three legs are spaced about 120 degrees apart. A cradle is pivoted to an end of one of the legs by a pivot having an axis disposed at right angles to the axis of the bore. This axis is hereinafter known as the pitch axis.

A transducer of the prior art is supported in the cradle by a pair of tension arms which are urged by a bias spring to independently move the opposed axial ends of the transducer radially outward into contact with the bore. The tension arms restrain the transducer from relative rotation about an axis parallel to the axis of the bore. The tension arms, may be manually adjusted about an axis parallel to the axis of the bore but displaced outward from the axis of the bore and, upon completion of the adjustment, may be manually locked in the selected angular position using, for example, one or more alignment screws. This axis parallel to the axis of the bore is hereinafter referred to as the roll axis.

Roll-axis alignment of an ultrasonic transducer conventionally employs a cut-and-try method in which an initial roll angle is manually selected and locked. A waxy substance such as, for example, crayon, is coated on the arcuate surface of the transducer. The transducer is then inserted into the axial bore. The three legs are expanded to bring the surface of the transducer into contact with the surface of the bore and the tube is rotated a few turns to remove the waxy substance from the transducer along its line of contact with the bore. The transducer is withdrawn from the bore and an improved roll-angle adjustment is performed based on the location of the line of contact. A high level of precision is required in the adjustment of the transducer roll angle in order to provide efficient transfer of ultrasonic energy into and out of the rotor and to enable accurate location of defects. Achieving the required precision with the above cut-and-try adjustment technique sometimes requires a long time to complete and necessitates the services of highly skilled personnel.

If a large number of bore radii must be accommodated in a turbine rotor, the above procedure must be repeated each time the transducer is changed. The alignment procedure thus may consume a substantial part of the overall ultrasonic testing schedule and may account for a substantial part of its cost.

OBJECTS AND SUMMARY OF THE INVENTION

It is thus an object of the invention to provide an improved ultrasonic transducer assembly which overcomes the deficiencies of the prior art.

It is a further object of the invention to provide an ultrasonic transducer assembly which automatically aligns the transducer about its roll axis.

It is another object of the invention to provide an improved ultrasonic transducer assembly which permits the changing of ultrasonic transducers rapidly and efficiently without manual alignment following each change.

Briefly stated, the invention is directed to a transducer assembly for maintaining a transducer in contact with, and in alignment with, a surface and includes a pair of opposed swivel bars, each of which is pivotably mounted to a cradle. The swivel bars are free to pivot about a roll axis. Two tension arms are pivotably mounted to one of the swivel bars. Each tension arm resiliently urges an end of the transducer into contact with the surface. One of the swivel bars supports two spaced-apart wheels whose contact with the surface is effective to rotate its swivel bar into a predetermined rotation about the roll axis. The transducer, being attached to the swivel bar by one of the tension arms is also rotated into a predetermined angle about the roll axis.

The above, and other objects, features and advantages of the present invention will become apparent from the following description read in conjunction with the accompanying drawings, in which like reference numerals designate the same elements.

BRIEF DESCRIPTION OF THE DRAWING

FIG. 2A is a side view of an ultrasonic transducer assembly of the prior art.

FIG. 2B is an end view of the transducer assembly of FIG. 2A.

FIG. 4A is a side view of the ultrasonic transducer assembly of FIG. 3 with the ultrasonic transducer used therewith shown in its fully outward non-operating position.

FIG. 4B is an end view of the ultrasonic transducer assembly of FIG. 4A.

FIG. 4C is an end view of the ultrasonic transducer assembly of FIGS. 4A and 4B in which the ultrasonic transducer is in its operative position in contact with a bore in a test object.

DETAILED DESCRIPTION OF A PREFERRED EMBODIMENT

Figure 1:
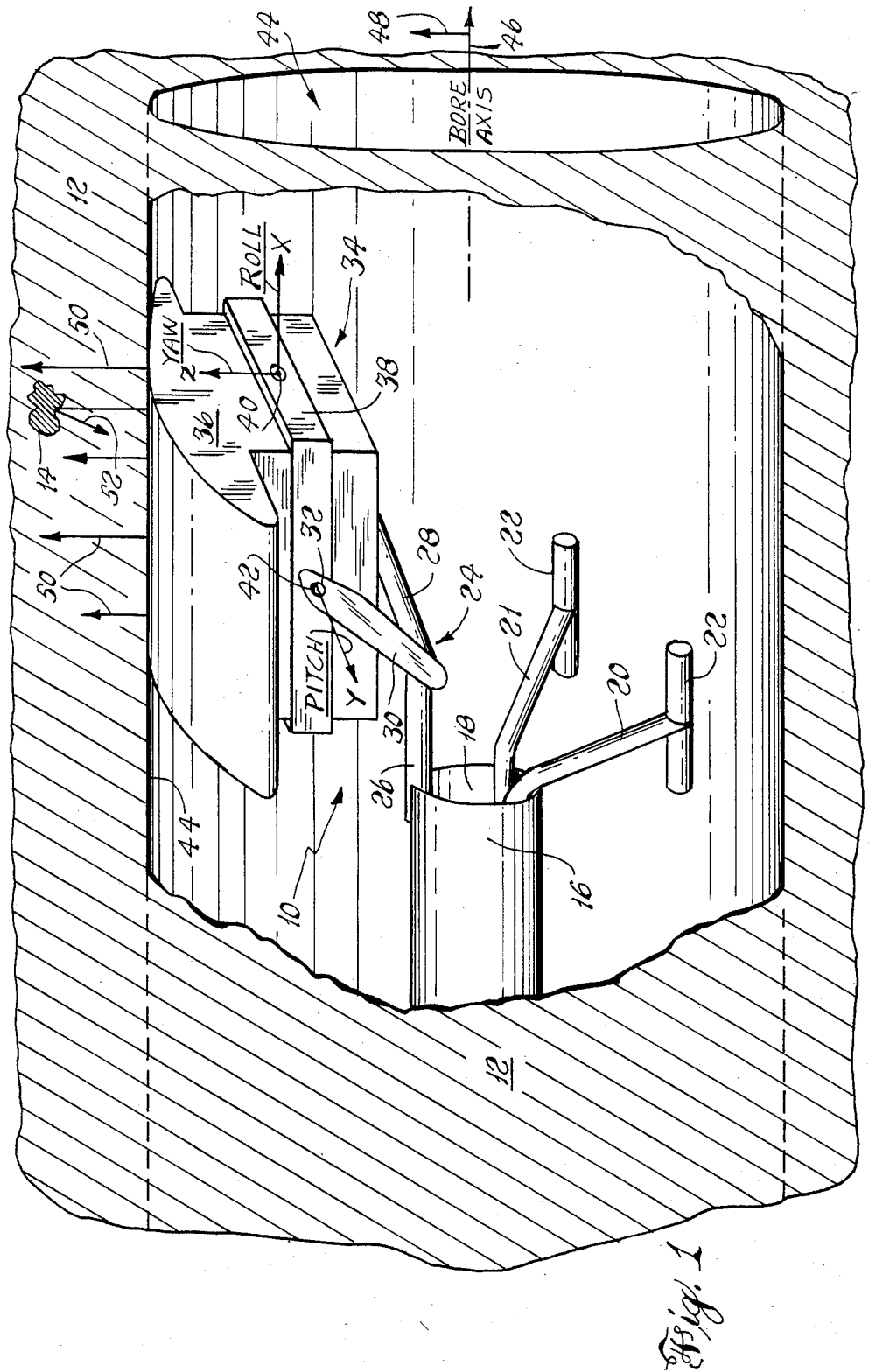
FIG. 1 is a cross-section of the bore of a test object showing an ultrasonic transducer assembly therein.

Referring to FIG. 1, there is shown, generally at 10, a simplified diagram of an ultrasonic testing device within its operative environment. Ultrasonic testing device 10 is used to test a test object 12 for defects therein, such as a flaw 14. Flaw 14 may be, for example, a crack, void or included foreign matter present in the test object. For concreteness of description, test object 12 is assumed to be a rotor of a steam turbine, but the application of the invention should not be considered to be limited to such an application.

Ultrasonic testing device 10 includes a central tube 16 having an opening 18 at the inner end thereof. Three angularly expandable legs 20, 21 and 26 extend about 120 degrees apart from opening 18. Legs 20 and 21 each have a foot 22 attached thereto. A forked arm 24 is rigidly affixed to the outer end of leg 26. Forked arm 24 includes a center bar 28 having a holding arm 30 rigidly attached to each end thereof. Each holding arm 30 has an opening 32 therein.

A transducer assembly 34 is pivotably supported by forked arm 24. Transducer assembly 34 includes a transducer 36 and a cradle 38. Transducer 36 is pivotably secured to cradle 38 at a pair of opposed pivot points 40 (only one of which is shown). An axis x passing through pivot points 40 is herein defined as a roll axis. Cradle 38 is pivotably secured to holding arm 30 at a pair of opposed pivot points 42 (only one of which is shown). Pivot points 42 are in operative engagement with openings 32 of holding arm 30. An axis y passing through pivot points 42 is herein defined as a pitch axis. A third axis z, disposed normal to a plane defined by the roll and pitch axes, is defined as the yaw axis.

A generally cylindrical bore 44 within test object 12 has a bore axis 46 and a radius 48. Legs 20, 21 and 26 are expanded to urge feet 22 and transducer assembly 34 into contact with the inner surface of bore 44. Ultrasonic testing device 10 is rotated in contact with the inner surface thereof while being axially moved along bore axis 46, thus describing a helical path along the length of bore 44. As transducer 36 traverses its helical path, it projects ultrasonic waves 50 into test object 12. The ultrasonic waves 50 travel in substantially straight lines within test object 12 until they are scattered or reflected by a defect, such as flaw 14. Some of the scattered or reflected waves 52 are returned to transducer 36 where they serve as an indication of the presence of flaw 14. The axial and rotational positions of transducer 36 at the time a reflected signal is received, as well as a measurement of the transit time of the ultrasonic signal through the test object 12, are employed to identify the location of flaw 14 in three dimensions. When a flaw is located, it may be removed or merely identified for follow-up surveillance.

FIGS. 2A and 2B illustrate two views of a prior art transducer assembly, generally shown at 54, which includes transducer 36 supported in a cradle 56. Cradle 56 includes a base 58 having openings 32' therein (only one of which is shown in FIG. 2A) for pivotable attachment to a forked arm 24 (see FIG. 1). A wheel mount 60 extends centrally upward at each end of cradle 56. A wheel 62 is rotatably affixed to each wheel mount 60. Each wheel 62 is located at approximately the same height relative to base 58, measured along the z axis. As best seen in FIG. 2B, first and second swivel bars mounts 64 (one of which is shown in FIG. 2B) are each pivotably mounted on a first pivot point 66 at opposed ends of cradle 56. First pivot points 66 coincide with roll axis x, as shown in FIG. 1. A pair of elliptical slots 78, in at least one swivel bar mount 64, each contains an alignment screw 80. The combination of pivot points 66 and alignment screws 80 permits adjustment and locking of the roll angle of swivel bar mount 64 as indicated by a first arrow 67.

A tension arm 70 is pivotably mounted to each swivel bar mount 64. Each tension arm 70 is pivotably about a respective pair of opposed second pivot points 68 at each end of swivel bar mount 64. A tension spring 72 urges the lower ends of tension arms 70 toward each other. The upper ends of each tension arm 70 are operably connected to transducer 36 at a respective pair of contact points 74, to independently urge its end of transducer 36 in the radially outward direction indicated by second arrow 76 and to rigidly restrain it from relative roll motion therewith. The independent outward urging of the ends of transducer 36 moves transducer 36 into uniform contact with the inner surface of bore 44 along a line of contact (not shown). The location of the line of contact on the surface of transducer 36 depends on the roll adjustment of transducer 36 in cradle 56. Such roll adjustment is performed by the adjustment and locking of swivel bar mounts 64.

The outward urging of forked arm 24 (FIG. 1) moves wheels 62 into rolling contact with bore 44 (FIG. 1). This establishes a predetermined datum from which the resilient urging of spring 72 produces and maintains a predictable contact pressure between transducer 36 and bore 44. The rolling contact of wheels 62 automatically maintains the correct pitch orientation of cradle 56. The independent radially outward resilient urging of the ends of transducer 36 automatically adjusts the pitch angle of transducer 36 about pitch axis y.

Using the above-described cut-and-try adjustment method, a preliminary adjustment of roll angle is made by loosening adjustment screws 80, rotating swivel bar mounts 64, with the attached transducer 36, to a trial position and tightening adjustment screws 80 to lock the roll position. After determining the position of the line of contact on the surface of transducer 36, the above roll-axis adjustment procedure is repeated as often as necessary to attain a roll-angle adjustment which coincides the line of contact with the desired position. The lengthy time and the high personnel skill level of personnel required to perform the above-described procedure reduces the desirability of such prior-art alignment techniques.

I have provided a new transducer assembly which automatically aligns an ultrasonic transducer against the inner surface of a bore around both the pitch and roll axes. The invention eliminates the need for realignment upon changing transducers.

Figure 3:
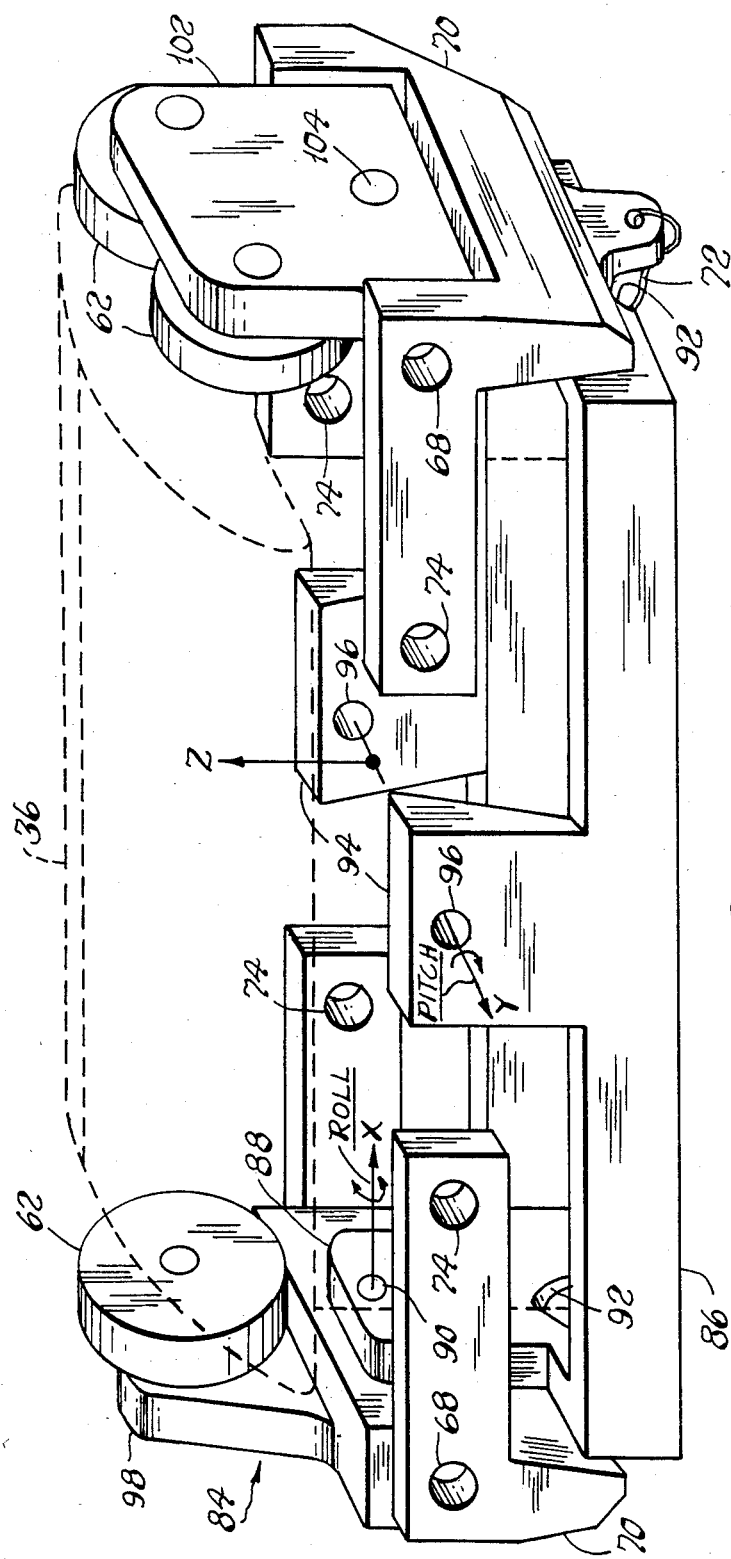
FIG. 3 is a perspective of an ultrasonic transducer assembly according to the invention, with an ultrasonic transducer used therewith shown in dotted line in order to avoid obscuring details thereof.

Referring now to FIG. 3, augmented by additional views in FIGS. 4A-4C, a transducer assembly 82 includes a cradle 84 and transducer 36, herein shown in dashed line. Cradle 84 includes a base 86 having a pair of swivel bar mounts 88 disposed on opposing ends thereof (only one swivel bar mount 88 is visible in FIG. 3). Swivel bar mounts 88 have pivots 90 and 104 therein. A line passing through pivots 90 and 104 defines roll axis x. A pair of arch-shaped openings 92 are disposed in cradle 84, one at each opposed end thereof. A pair of holding arm supports 94, each having a pivot opening 96, are centrally disposed on the sides of cradle 84 for pivotable attachment of forked arm 24 (see FIG. 1). A line passing through pivot openings 96 defines pitch axis y.

A first pivot alignment block 98 is disposed adjacent a first swivel bar mount 88. A pivot 90 engages first pivot alignment block 98 to permit relative pivoting of first pivot alignment block 98 and swivel bar mount 88. A second pivot alignment block 102 is disposed adjacent the other swivel bar mount 88 (hidden in FIG. 3 but visible in FIG. 4A). Pivot 104 engages second pivot alignment block 102 to permit relative pivoting of second pivot alignment block 102 and its adjacent swivel bar mount. First pivot alignment block 98 and second pivot alignment block 102 are capable of free rotation about roll axis x on pivots 90 and 104.

First pivot alignment block 98 supports a single wheel 62 disposed at a first distance or height, measured along the z axis, from roll axis x. Second pivot alignment block 102 supports a pair of wheels 62 disposed at a second distance, less than the first distance, measured along the z axis, from roll axis x. The pair of wheels 62 supported by second pivot alignment block 102 are further disposed at equal distances on either side of roll axis x.

First and second tension arms 70 are pivotably mounted to first and second pivot alignment blocks 98 and 102 using second pivot points 68. The lower ends of tension arms 70 are urged toward each other by a spring 72. Transducer 36 is pivotably mounted in cradle 84 by two opposed contact points in each tension arm 70.

The two wheels 62 on second pivot alignment block 102, upon contacting the interior surface of bore 44, automatically rotate second pivot alignment block 102 about roll axis x until second pivot alignment block 102 arrives at a predetermined roll angle. Transducer 36 is affixed to second pivot alignment block 102 in a manner which prevents relative rotation thereof about roll axis x. Thus the automatic roll alignment of second pivot alignment block 102 performs the automatic roll alignment of transducer 36. First pivot alignment block 98, being affixed to transducer 36 in a manner which prevents relative roll-angle rotation therebetween, is also automatically rotated into a predetermined roll angle. Thus, whenever transducer 36 is urged into contact with the surface of bore 44, the roll angle of transducer 36 is automatically attained without the need for cut-and-try manual adjustment.

It will be readily appreciated by those of ordinary skill in the art, that the precise relative disposition of wheels 62 on first pivot alignment block 98 and second pivot alignment block 102 is not critical, nor is it critical that there be exactly three such wheels 62. It is only critical that there be a sufficient number thereof placed in positions effective to align one end of the transducer about the roll axis x and to support the other end of cradle 84 at a height substantially equal to the height achieved by the two wheels at the other end.

It will be evident to one skilled in the art that one or more of wheels 62 may be eliminated without departing from the spirit and scope of the invention. For example, the single wheel 62 on first pivot alignment block 98 may be replaced by a non-rolling contact element such as a boss (not shown). The boss may be a simple continuation of first pivot alignment block 98 which extends far enough upward to provide suitable support for its end of cradle 84. The boss may be coated with a low-friction material if desired to lubricate a sliding contact with the surface of bore 44. In a similar manner, one skilled in the art would recognize that the pair of wheels on second pivot alignment block 102 could be replaced with a pair of non-rolling contact elements (not shown) positioned in a manner similar to the positioning of wheels 62 and effective for automatically achieving roll alignment and for supporting the end of cradle 54.

Having described specific preferred embodiments of the invention with reference to the accompanying drawings, it is to be understood that the invention is not limited to those precise embodiments and that various changes and modifications may be effected therein by one skilled in the art without departing from the scope or spirit of the invention as defined in the appended claims.

What is claimed is:

1. Apparatus for positioning an object having a first surface with a predetermined radius of curvature in alignment with a second surface having a second predetermined radius of curvature, comprising:

first means for pivoting said object about a roll axis;
   second means for pivoting said object about a pitch axis;
   said second means including means for moving the first surface said object into contact with said second surface; and
   said first means including means for automatically pivoting said object into a predetermined rotation about said roll axis, such that a predetermined portion of said second surface contacts said first surface of said object.

2. Apparatus for positioning an object in alignment with a surface, comprising:
   first means including at least first and second pivot alignment blocks, said first means for pivoting said object about a roll axis;
   second means for pivoting said object about a pitch axis;
   said second means including means for moving said object into contact with said surface; and
   said first means including means for automatically pivoting said object into a predetermined rotation about said roll axis.

3. Apparatus in accordance with claim 2 wherein said first pivot alignment blocks includes means for supporting at least first and second contact devices, said at least first and second contact devices being positioned to contact said surface and effective for pivoting said object into said predetermined rotation.

4. Apparatus in accordance with claim 3 wherein said at least first and second contact devices include at least first and second wheels.

5. Apparatus in accordance with claim 3 wherein said means for supporting at least first and second contact devices includes first and second pivot points disposed equally about said roll axis.

6. Apparatus in accordance with claim 5 wherein said first and second pivot points are disposed at a first height, said first height being measured in a direction normal to a plane defined by said roll axis and said pitch axis; and
   said second pivot alignment block includes a third contact device disposed at a second height from said plane, said second height being greater than said first height.

7. Apparatus according to claim 6 wherein said third contact device is a wheel.

8. Apparatus in accordance with claim 2 wherein said means for automatically pivoting said object includes at least first and second wheels positioned at a first height relative to a plane defined by said roll axis and said pitch axis, said at least first and second wheels being positioned to contact said surface when said object is in contact therewith.

9. Apparatus in accordance with claim 8 wherein said means for automatically pivoting said object further includes a single wheel at a second height relative to said plane, said single wheel being positioned to contact said surface when said at least first and second wheels are in contact with said surface; and
   said second height is greater than said first height.

10. A transducer assembly for maintaining a transducer in contact with a surface, said assembly comprising:
    a cradle having a roll axis and a pitch axis;
    a first swivel bar disposed at a first end of said cradle;
    means for pivotably mounting said first swivel bar to said cradle;
    said means for pivotably mounting includes means for permitting pivoting movement of said first swivel bar about said roll axis;
    said first swivel bar including first and second pivot points disposed at a first height relative to a plane defined by said roll and pitch axes of said cradle, said first and second pivot points being further disposed at equal distances about said roll axis of said cradle;
    first and second spaced-apart contact devices affixed to said first and second pivot points respectively, said first and second contact devices contacting said surface when said transducer contacts said surface, said first and second contact devices being effective to pivot said first swivel bar into a predetermined angle about said roll axis when said first and second contact devices are in contact with said surface;
    at least a first tension arm pivotably mounted to said first swivel bar and including means for permitting pivotal movement about an axis parallel to said pitch axis; and
    means for pivotably affixing said transducer to said at least a first tension arm, said means for pivotably affixing including means for permitting relative rotation of said transducer and said at least a first tension arm about an axis parallel to said pitch axis and for preventing relative rotation therebetween about said roll axis.

11. A transducer assembly in accordance with claim 10 further comprising:
    a second swivel bar disposed at a second end of said cradle;
    said second swivel bar being pivotably mounted to said cradle, and including means for permitting pivoting movement thereof about said roll axis;
    said second swivel bar including a single pivot point disposed at a second height relative to said plane, said second height being greater than said first height;
    a third contact device affixed to said single pivot point;
    a second tension arm pivotably mounted to said second swivel bar, and including means for permitting pivotal movement about an axis parallel to said pitch axis; and
    means for pivotably affixing said transducer to said second tension arm.

12. A transducer assembly in accordance with claim 11 wherein at least one of said at least first and second tension arms includes means for resiliently urging said transducer into said contact with said surface.

13. A transducer assembly in accordance with claim 12 wherein said means for resiliently urging includes a spring urging an end of said first tension arm and an end of said second tension arm toward each other.

14. A transducer assembly for maintaining a transducer in contact with an inner surface of a bore, said inner surface being generally concave and said transducer having a generally arcuate upper surface, said arcuate upper surface being generally complementary to said inner surface comprising:
    a cradle having a roll axis and a pitch axis;
    a first swivel bar disposed at a first end of said cradle;
    said first swivel bar being pivotably mounted to said cradle and including means for permitting pivoting movement about said roll axis;
    said first swivel bar including first and second spaced-apart pivot points disposed at a first height relative to a plane defined by said roll and pitch axes of said cradle, said first and second spaced-apart pivot points being further disposed at equal distances on either side of said roll axis;
    a first tension arm pivotably mounted to said first swivel bar, and including means for permitting pivotal movement thereof about an axis parallel to said pitch axis;

a second swivel bar disposed at a second end of said cradle;

said second swivel bar being pivotably mounted to said cradle, and including means for permitting pivoting movement thereof about said roll axis;

said second swivel bar including a single pivot point disposed at a second height relative to said plane, said second height being greater than said first height;

a second tension arm pivotably mounted to said second swivel bar, and including means for permitting pivotal movement about an axis parallel to said pitch axis;

first and second means for pivotably affixing said first and second tension arms to spaced-apart points on said transducer;

said first and second means for pivotably affixing including means for permitting relative rotation of said transducer and at least said first swivel bar about an axis parallel to said pitch axis and for preventing relative rotation of said transducer and at least said first swivel bar about said roll axis;

said first and second spaced-apart pivot points contacting said surface and being effective for pivoting said first swivel bar into a predetermined angle about said roll axis whereby said transducer is also pivoted into a predetermined angle about said roll axis.

15. A transducer assembly in accordance with claim 14 wherein each of said first and second spaced-apart pivot points includes a wheel;

each of said wheels contacting a point on said inner surface when said transducer is in contact with said inner surface; and points on said inner surface contacted by said first and second spaced-apart pivot points defining a chord of said bore, a center point of said chord intersecting a first radius of said bore.

16. A transducer assembly in accordance with claim 15 wherein said single pivot point of said second swivel bar is disposed along said first radius of said bore.

17. A transducer assembly in accordance with claim 16 wherein said single pivot point includes a wheel;

said wheel on said second swivel bar contacting a point on said inner surface of said bore when said transducer is in contact therewith.

* * * * *